United States Patent [19]

Kortenbach et al.

[11] Patent Number: 5,897,507
[45] Date of Patent: Apr. 27, 1999

[54] BIOPSY FORCEPS INSTRUMENT HAVING IRRIGATION AND ASPIRATION CAPABILITIES

[75] Inventors: Juergen Andrew Kortenbach, Miami Springs; Vincent Turturro, Miramar; Michael Sean McBrayer, Miami; Peter Kratsch, Sunrise, all of Fla.

[73] Assignee: Symbiosis Corporation, Miami, Fla.

[21] Appl. No.: 08/756,260

[22] Filed: Nov. 25, 1996

[51] Int. Cl.$^6$ .................................................... A61B 10/00
[52] U.S. Cl. ......................... 600/562; 600/563; 600/564; 600/565; 600/566; 606/127; 606/205; 606/206; 606/207; 606/170
[58] Field of Search .................................... 600/562, 563, 600/564, 565, 570, 571; 606/110, 114, 127, 205–207, 167, 170, 174; 30/115, 116, 124, 134; 604/22

[56] References Cited

U.S. PATENT DOCUMENTS

| | | |
|---|---|---|
| Re. 33,258 | 7/1990 | Onik et al. . |
| 2,708,437 | 5/1955 | Hutchins . |
| 3,173,414 | 3/1965 | Guillant . |
| 3,289,669 | 12/1966 | Dwyer et al. . |
| 3,401,684 | 9/1968 | Dremann . |
| 3,590,808 | 7/1971 | Muller . |
| 3,732,858 | 5/1973 | Banko . |
| 3,964,468 | 6/1976 | Schulz . |
| 3,980,086 | 9/1976 | Kletschka et al. . |
| 3,989,033 | 11/1976 | Halpern et al. . |

(List continued on next page.)

FOREIGN PATENT DOCUMENTS

| | | |
|---|---|---|
| 0 317 526 | 5/1989 | European Pat. Off. . |
| 526115 | 2/1993 | European Pat. Off. . |
| 4135554 | 5/1992 | Japan . |
| 07516 | 5/1992 | WIPO . |

OTHER PUBLICATIONS 510k application communications between Department of Health & Human Services and William Z. Kolozsi, M.D., relating to Triton Technologies Multiple Biopsy Device, dated Mar. 11, 1991 through May 1, 1991, 27 pages.
Quinton, "Model 4.7mm Multipurpose Biopsy Tube" operator manual, 10 pages.

Primary Examiner—Richard J. Apley
Assistant Examiner—Justine R. Yu
Attorney, Agent, or Firm—Finnegan, Henderson, Farabow, Garrett & Dunner, L.L.P.

[57] ABSTRACT

A biopsy forceps instrument is provided having a proximal actuation handle, a flexible multi-lumen tubular member, at least one control member extending through a lumen, an irrigation means, an aspiration means, and a distal assembly. The proximal actuation handle includes a shaft and a spool slidably mounted on the shaft. The actuation handle is coupled to the proximal ends of both the flexible tubular member and the control member. Lumens of the tubular member form irrigation and aspiration conduits. The distal assembly includes a hollow jaw cup coupled to the aspiration conduit and a hollow movable jaw coupled adjacent the irrigation conduit. The movable jaw is coupled to the control member, such that actuation of the actuation handle moves the movable jaw relative to the jaw cup. Moving the hollow jaws into a closed position provides a substantially fluidtight coupling between the irrigation and aspiration conduits. The actuation handle is also provided with an assembly to control irrigation to and aspiration from the distal assembly. A proximal sample chamber having a removable screen is provided for filtering tissue samples aspirated from the distal assembly. The jaws are activated to cut a tissue sample and the irrigation and aspiration means are activated to move the sample into the sample chamber for retrieving the sample without removing the instrument from a patient.

29 Claims, 13 Drawing Sheets

U.S. PATENT DOCUMENTS

| | | |
|---|---|---|
| 3,989,049 | 11/1976 | Yoon . |
| 3,992,565 | 11/1976 | Gatfield . |
| 4,014,333 | 3/1977 | McIntyre . |
| 4,200,111 | 4/1980 | Harris . |
| 4,282,884 | 8/1981 | Boebel . |
| 4,445,517 | 5/1984 | Feild . |
| 4,519,385 | 5/1985 | Atkinson et al. . |
| 4,522,206 | 6/1985 | Whipple et al. . |
| 4,617,013 | 10/1986 | Betz . |
| 4,632,110 | 12/1986 | Sanagi . |
| 4,644,951 | 2/1987 | Bays . |
| 4,646,751 | 3/1987 | Maslanka . |
| 4,651,753 | 3/1987 | Lifton . |
| 4,662,371 | 5/1987 | Whipple et al. . |
| 4,681,123 | 7/1987 | Valtchev . |
| 4,693,257 | 9/1987 | Markham . |
| 4,712,545 | 12/1987 | Honkanen . |
| 4,759,349 | 7/1988 | Betz et al. . |
| 4,763,668 | 8/1988 | Macek et al. . |
| 4,776,840 | 10/1988 | Freitas et al. . |
| 4,785,825 | 11/1988 | Romaniuk et al. . |
| 4,881,550 | 11/1989 | Kothe . |
| 4,909,782 | 3/1990 | Semm et al. . |
| 4,919,152 | 4/1990 | Ger . |
| 4,924,851 | 5/1990 | Ognier et al. . |
| 4,944,093 | 7/1990 | Falk . |
| 4,950,278 | 8/1990 | Sachse et al. . |
| 4,953,559 | 9/1990 | Salerno . |
| 4,966,162 | 10/1990 | Wang . |
| 4,971,067 | 11/1990 | Bolduc et al. . |
| 4,973,311 | 11/1990 | Iwakoshi et al. . |
| 4,976,723 | 12/1990 | Schad . |
| 4,986,825 | 1/1991 | Bays et al. . |
| 5,082,000 | 1/1992 | Picha et al. . |
| 5,085,658 | 2/1992 | Meyer . |
| 5,106,364 | 4/1992 | Hayafuji et al. . |
| 5,112,346 | 5/1992 | Hiltebrandt et al. . |
| 5,125,910 | 6/1992 | Freitas . |
| 5,147,292 | 9/1992 | Kullas et al. . |
| 5,152,780 | 10/1992 | Honkanen et al. . |
| 5,160,343 | 11/1992 | Brancel et al. . |
| 5,171,255 | 12/1992 | Rydell . |
| 5,172,700 | 12/1992 | Bencini et al. . |
| 5,176,629 | 1/1993 | Kullas et al. . |
| 5,186,714 | 2/1993 | Boudreault et al. . |
| 5,195,533 | 3/1993 | Chin et al. . |
| 5,195,958 | 3/1993 | Phillips . |
| 5,195,959 | 3/1993 | Smith . |
| 5,197,963 | 3/1993 | Parins . |
| 5,197,968 | 3/1993 | Clement . |
| 5,209,747 | 5/1993 | Knoepfler . |
| 5,217,460 | 6/1993 | Knoepfler . |
| 5,219,357 | 6/1993 | Honkanen et al. . |
| 5,230,704 | 7/1993 | Moberg et al. . |
| 5,244,459 | 9/1993 | Hill . |
| 5,251,641 | 10/1993 | Xavier . |
| 5,285,795 | 2/1994 | Ryan et al. . |
| 5,286,255 | 2/1994 | Weber . |
| 5,300,087 | 4/1994 | Knoepfler . |
| 5,312,327 | 5/1994 | Bales et al. . |
| 5,312,400 | 5/1994 | Bales et al. . |
| 5,314,406 | 5/1994 | Arias et al. . |
| 5,325,866 | 7/1994 | Krzyzanowski . |
| 5,336,238 | 8/1994 | Holmes et al. . |
| 5,344,428 | 9/1994 | Griffiths . |
| 5,456,689 | 10/1995 | Kresch et al. . |
| 5,471,992 | 12/1995 | Banik et al. . |
| 5,527,332 | 6/1996 | Clement . |
| 5,538,008 | 7/1996 | Crowe . |
| 5,542,432 | 8/1996 | Slater et al. . |
| 5,551,448 | 9/1996 | Matula et al. . |
| 5,562,102 | 10/1996 | Taylor . |
| 5,562,640 | 10/1996 | McCabe et al. . |
| 5,569,299 | 10/1996 | Dill et al. . |
| 5,573,008 | 11/1996 | Robinson et al. . |
| 5,575,293 | 11/1996 | Miller et al. . |
| 5,593,416 | 1/1997 | Donahue . |
| 5,595,185 | 1/1997 | Erlich . |
| 5,601,585 | 2/1997 | Banik et al. . |
| 5,603,724 | 2/1997 | O'Connor . |
| 5,607,391 | 3/1997 | Klinger et al. . |
| 5,636,639 | 6/1997 | Turturro et al. . |
| 5,638,827 | 6/1997 | Palmer et al. . |
| 5,645,075 | 7/1997 | Palmer et al. . |
| 5,683,359 | 11/1997 | Farkas et al. . |
| 5,683,388 | 11/1997 | Slater et al. . |

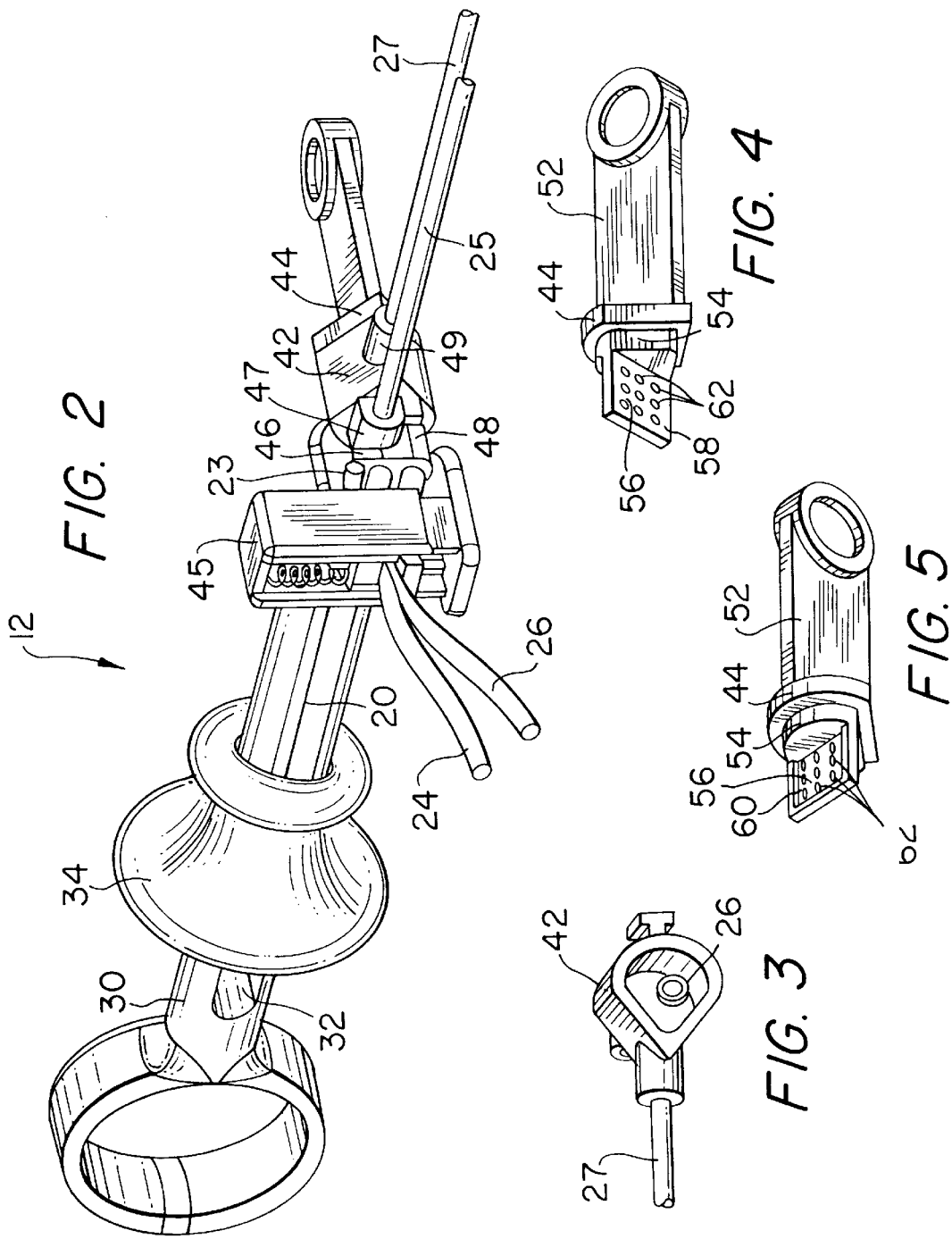

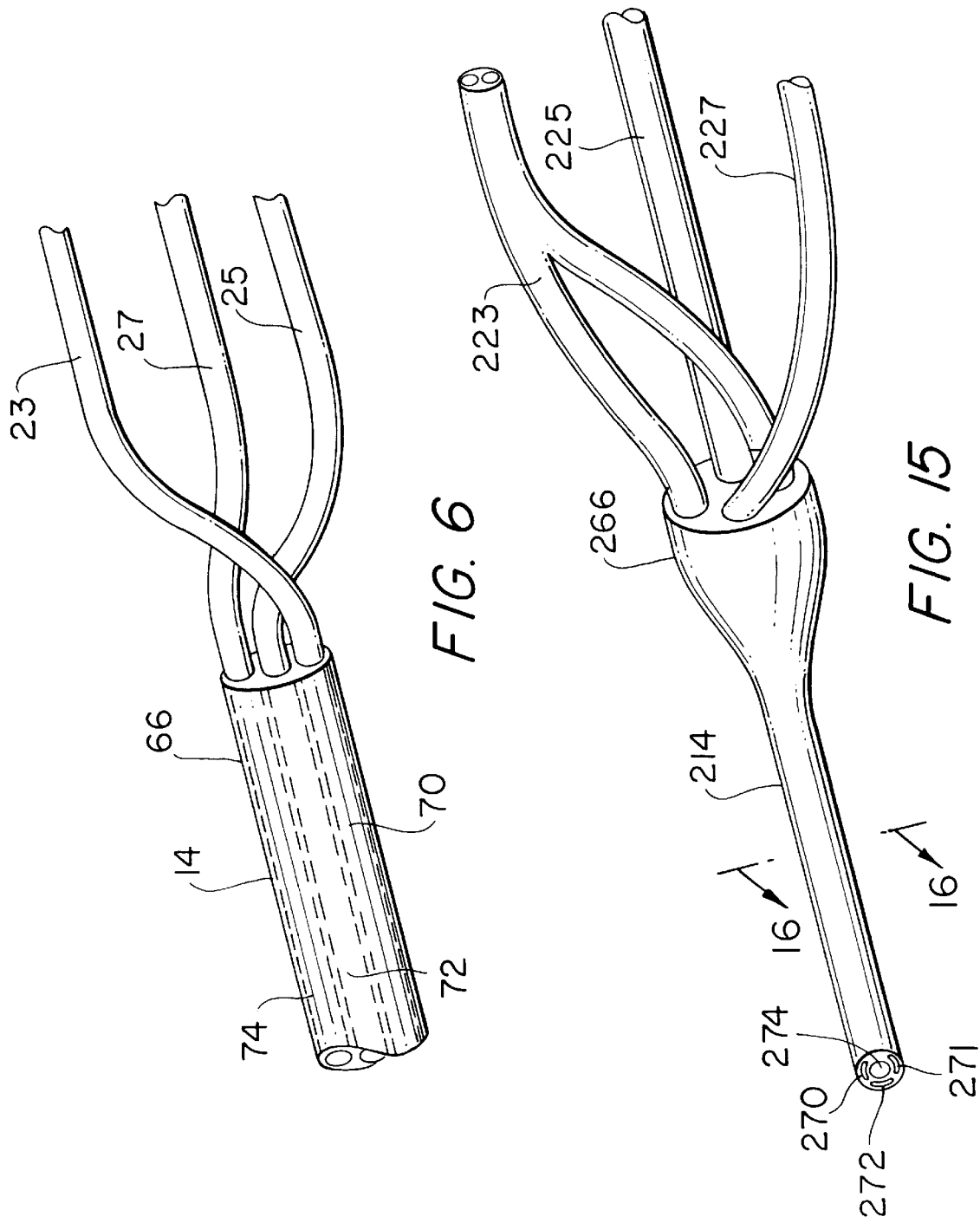

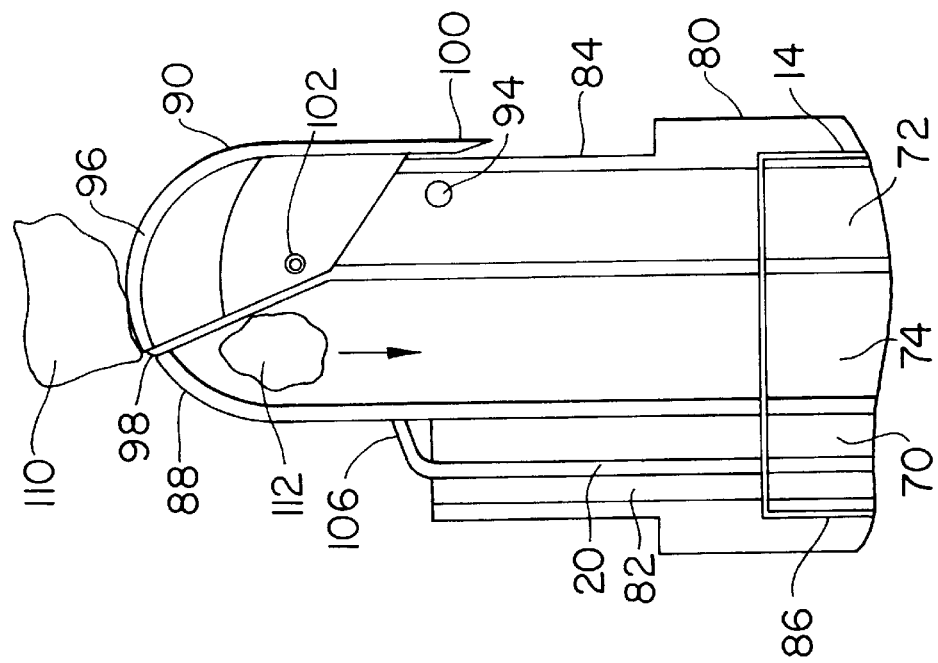
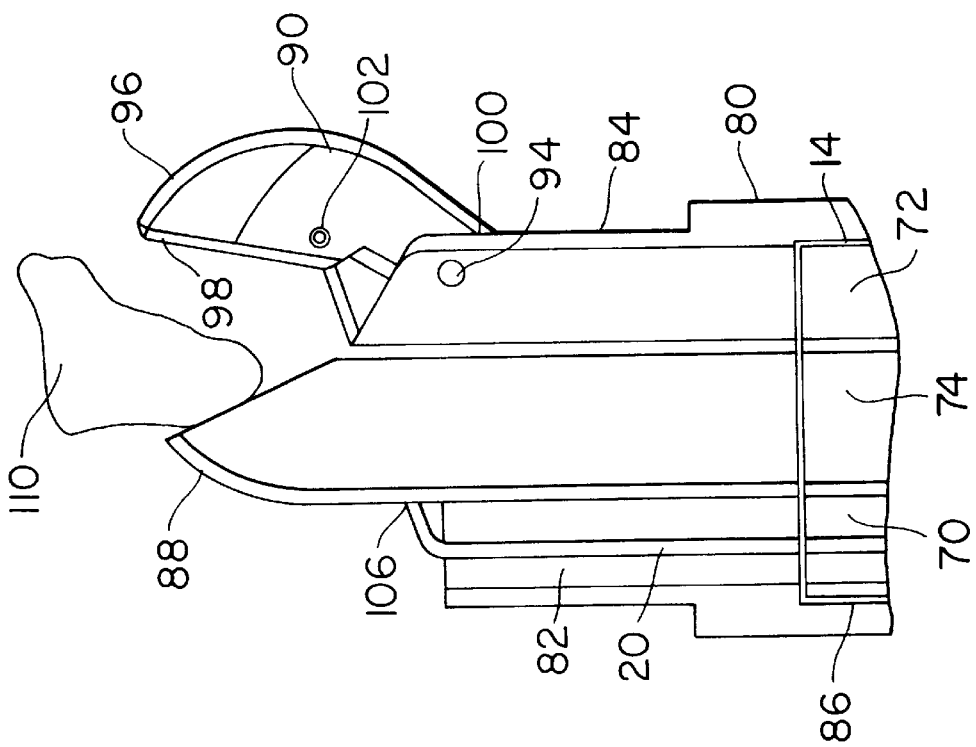

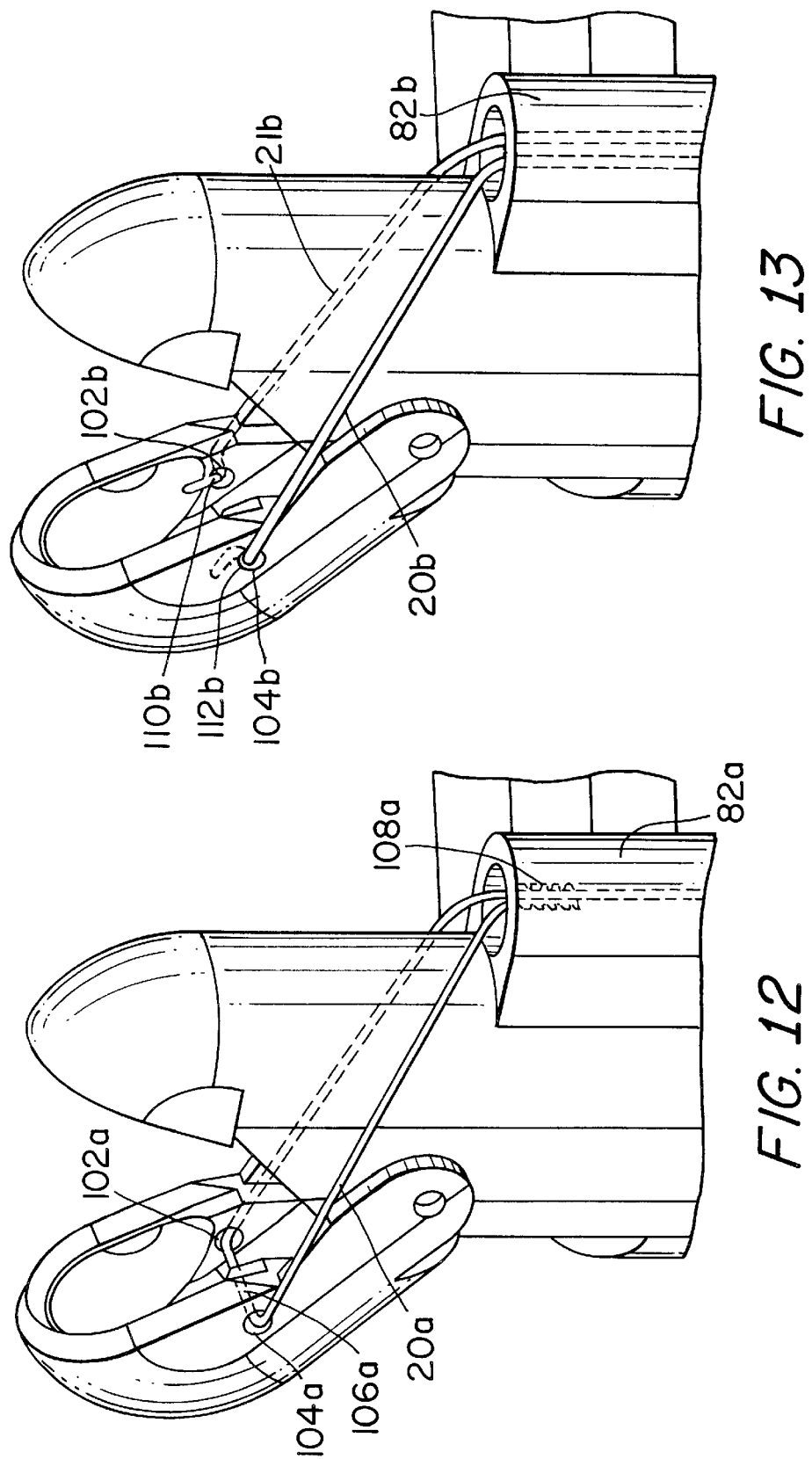

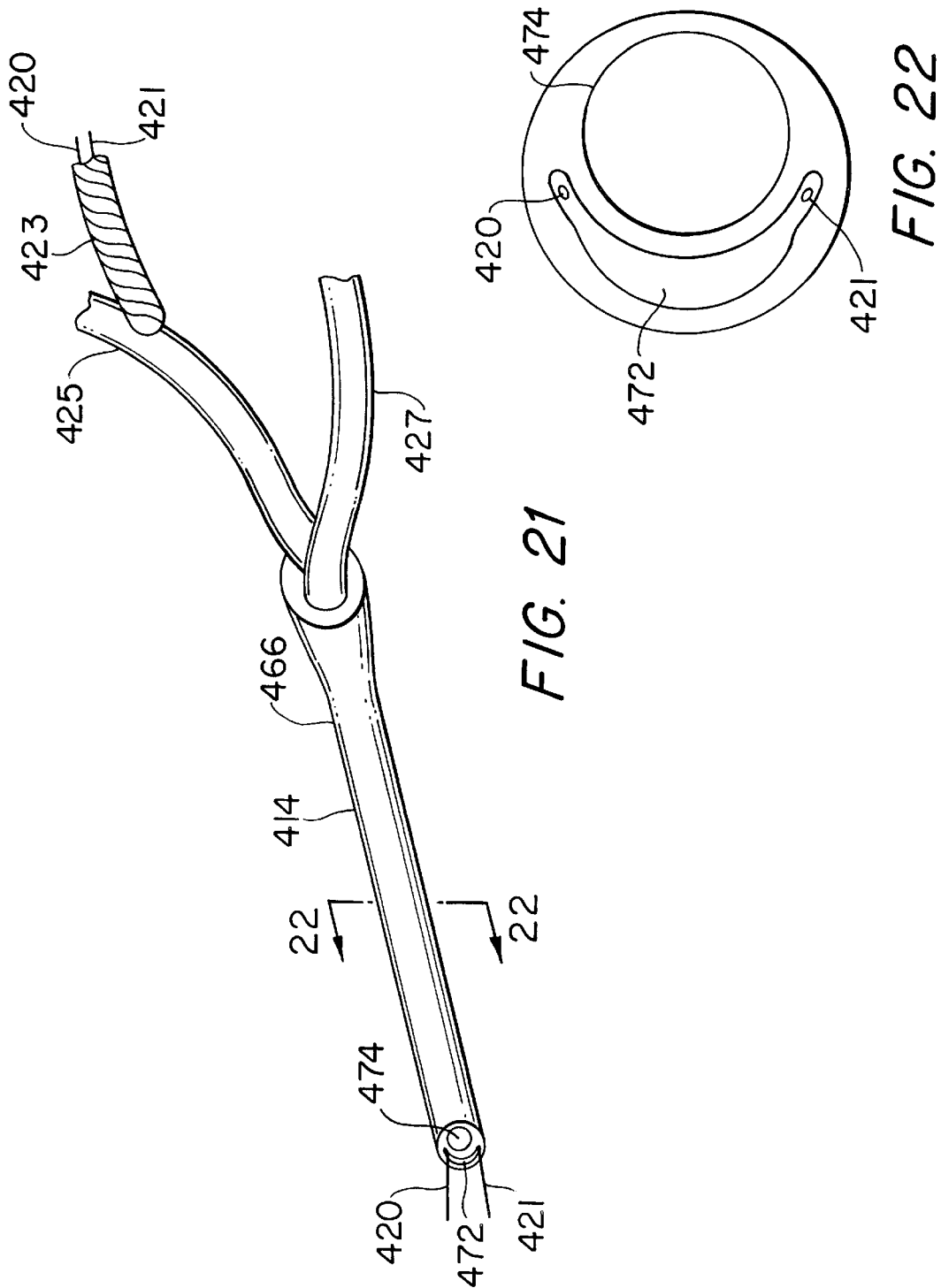

BIOPSY FORCEPS INSTRUMENT HAVING IRRIGATION AND ASPIRATION CAPABILITIES

BACKGROUND OF THE INVENTION

1. Field of the Invention

This invention relates broadly to endoscopic surgical instruments. More particularly, this invention relates to an endoscopic biopsy forceps instrument with means for facilitating sample removal without withdrawal of the biopsy forceps instrument from an endoscope.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope. Thus, several known multiple sample biopsy instruments are precluded from use with an endoscope because of their size and rigidity. These include the "punch and suction type" instruments disclosed in U.S. Pats. No. 3,989,033 to Halpern et al. and No. 4,522,206 to Whipple et al. Both of these devices have a hollow tube with a punch at the distal end and a vacuum source coupled to the proximal end. A tissue sample is cut with the punch and suctioned away from the biopsy site through the hollow tube. It is generally recognized, however, that dry suctioning tissue samples (i.e., without the use of an irrigating fluid) through a long narrow flexible bioptome is virtually impossible.

Efforts have been made to provide multiple sampling ability to an instrument which must traverse the narrow lumen of an endoscope. These efforts have concentrated on providing a cylindrical storage space at the distal end of the instrument wherein several tissue samples can be accumulated before the instrument is withdrawn from the endoscope. U.S. Pat. No. 4,651,753 to Lifton, for example, discloses a rigid cylindrical member attached to the distal end of a first flexible tube. The cylindrical member has a lateral opening and a concentric cylindrical knife blade is slidably mounted within the cylindrical member. A second flexible tube, concentric to the first tube is coupled to the knife blade for moving the knife blade relative to the lateral opening in the cylindrical member. A third flexible tube having a plunger tip is mounted within the second flexible tube and a vacuum source (a syringe) is coupled to the proximal end of the third tube. A tissue sample is taken by bringing the lateral opening of the cylindrical member upon the biopsy site, applying vacuum with the syringe to draw tissue into the lateral opening, and pushing the second flexible tube forward to move the knife blade across the lateral opening. A tissue sample is thereby cut and trapped inside the cylindrical knife within the cylindrical member. The third flexible tube is then pushed forward moving its plunger end against the tissue sample and pushing it forward into a cylindrical storage space at the distal end of the cylindrical member. Approximately six samples can be stored in the cylindrical member, after which the instrument is withdrawn from the endoscope. A distal plug on the cylindrical member is removed and the six samples are collected by pushing the third tube so that its plunger end ejects the samples.

The device of the Lifton patent suffers from several recognizable drawbacks. First, it is often difficult to obtain a tissue sample laterally of the device. Second, in order to expedite the obtaining of a lateral sample, a syringe is used to help draw the tissue into the lateral opening. However, this causes what was once a two-step procedure (position and cut), to become a three-step procedure (position, suction, cut). In addition, the use of a syringe requires an additional hand. Third, the Lifton patent adds a fourth step to the biopsy procedure by requiring that the tissue sample be pushed into the storage space. Thus, in all, the Lifton patent requires substantial effort on the part of the surgeon and an assistant and much of this effort is involved in pushing tubes, an action which is counter-intuitive to classical biopsy sampling. The preferred mode of operation of virtually all endoscopic tools is that a gripping action at the distal end of the instrument is effected by a similar action at the proximal end of the instrument. Classical biopsy forceps jaws are closed by squeezing a manual actuation member in a syringe-like manner.

A more convenient endoscopic multiple sample biopsy device is disclosed in U.S. Pat. No. 5,171,255 to Rydell. Rydell provides a flexible endoscopic instrument with a knife-sharp cutting cylinder at its distal end. A coaxial anvil is coupled to a pull wire and is actuated in the same manner as conventional biopsy forceps. When the anvil is drawn into the cylinder, tissue located between the anvil and the cylinder is cut and pushed into a storage space within the cylinder. Several samples may be taken and held in the storage space before the device is withdrawn from the endoscope. While the device of Rydell is effective in providing a multiple sample tool where each sample is obtained with a traditional two-step procedure (position and cut), it is still limited to lateral cutting which is often problematic. Traditional biopsy forceps provide jaws which can grasp tissue frontally or laterally. Even as such, it is difficult to position the jaws about the tissue to be sampled. Lateral sampling is even more difficult.

A multiple sample biopsy forceps of a more traditional form is disclosed in co-owned U.S. Pat. No. 5,542,432 to Slater et al. Slater et al. discloses an endoscopic multiple sample biopsy forceps having a jaw assembly which includes a pair of opposed toothed jaw cups each of which is coupled by a resilient arm to a base member. The base member of the jaw assembly is mounted inside a cylinder and axial movement of one of the jaw assembly and cylinder relative to the other draws the arms of the jaws into the cylinder or moves the cylinder over the arms of the jaws to bring the jaw cups together in a biting action. The arms of the jaws effectively form a storage chamber which extends proximally from the lower jaw cup and prevents accumulated biopsy samples from being squeezed laterally out from between the jaws during repeated opening and closing of the jaws and the lower jaw cup enhances movement of the biopsy samples into the storage chamber. The device can hold up to four samples before it must be retrieved out of the endoscope. However, in some biopsy procedures it is sometimes desirous to retrieve more. In addition, it has been found that samples within the chamber can stick together and make determinations of which sample came from which biopsy site somewhat difficult.

U.S. Pat. No. 5,538,008 to Crowe discloses a multiple sample bioptome which purports to take several samples and to transfer each sample by water pressure through a duct to the proximal end of the instrument, where each sample can be individually retrieved. The device includes a plastic jaw set biased in an open position and coupled to the distal end of an elongate tube, up to seven feet long. The tube defines a duct. A sleeve extends over the tube and a water flow passage is provided between the tube and the sleeve. An aperture is provided in the tube to permit the water flow passage to meet the duct at the distal end of the tube. Withdrawing the tube into the sleeve is disclosed to force the jaws closed and enable a sample to be cut from tissue and lodge in the duct. The water flow passage is disclosed to enable water to flow under pressure from the proximal end of passage to the distal end of the passage, through the aperture and into the distal end of the duct and to be aspirated to the proximal end of the duct, thereby transferring with it any sample contained in the duct to the proximal end where the sample can be retrieved.

While on paper the Crowe device is appealing, in practice the design is impractical and flawed. For example, it would be very difficult, if not impossible, to slide the elongate tube, up to seven feet in length, relative to a sleeve of substantially the same length. It would also be difficult to maintain an unobstructed water flow passage between the tube and sleeve as the tube and sleeve curve and bend through the body. Furthermore, in order for the jaws to cut a tissue sample, the tube and jaws must be drawn into the sleeve, thereby undesirably pulling the jaws away from the tissue to be sampled.

SUMMARY OF THE INVENTION

It is therefore an object of the invention to provide an endoscopic biopsy forceps instrument which permits numerous tissue samples to be taken from a patient without removing the forceps from within the patient.

It is another object of the invention to provide an endoscopic biopsy forceps instrument which can individually retrieve each of several tissue samples from the forceps without removing the forceps from the patient.

It is a further object of the invention to provide an endoscopic biopsy forceps instrument which can take tissue samples located either distally or laterally relative to the instrument.

It is an additional object of the invention to provide an endoscopic biopsy forceps instrument which irrigates the forceps and aspirates tissue samples contained therein.

It is also an object of the invention to provide an endoscopic biopsy forceps instrument which includes a reservoir to catch samples aspirated through the instrument.

In accord with these objects which will be discussed in detail below, an endoscopic biopsy forceps instrument is provided and generally includes a proximal actuation handle, a distal forceps assembly, a control member coupled to the proximal actuation handle and the distal forceps assembly, and a flexible multi-lumen tubular member having an irrigation conduit, an aspiration conduit, and a control conduit which receives the control member.

According to a preferred embodiment of the invention, the proximal actuation handle includes a shaft and a spool slidably mounted on the shaft. The actuation handle is also provided with a proximal irrigation passage, a sample chamber, a sample catch member, and a pinch valve which regulates irrigation and aspiration. The proximal irrigation passage is coupled to the irrigation conduit and to an irrigation coupling tube. The sample chamber is coupled to the aspiration conduit and to an aspiration coupling tube. The sample catch member includes a screen which is inserted into the sample chamber and filters out tissue samples from the aspirated fluid. The irrigation coupling tube and the aspiration coupling tube extend through the pinch valve which operates to control the flow of fluid through the tubes. The actuation handle is coupled to the proximal ends of both the flexible tubular member and the control member and moves the control member relative to the tubular member.

The distal assembly is coupled to the distal end of the tubular member and includes a hollow jaw cup coupled over the distal end of the aspiration conduit and a hollow movable jaw pivotally coupled adjacent the irrigation conduit. The jaw cup is preferably formed from a hard plastic and has a blunt cutting surface, while the movable jaw is preferably a metal jaw with a sharp cutting edge. The movable jaw is further coupled to the control member, such that actuation of the actuation handle moves the movable jaw relative to the jaw cup, and thereby moves the jaws from an open position to a closed position. Moving the hollow jaws to a closed position provides a substantially fluidtight coupling between the irrigation and aspiration conduits.

It will be appreciated that the distal end of the instrument is brought into contact with tissue of which a sample is required and the actuation handle is actuated to close the jaws and cut off a tissue sample. With the jaws in a closed position, water is irrigated through the irrigation conduit to the jaws at the distal end of the instrument and aspirated from the jaws to the proximal end of the instrument through the aspiration conduit, such that the sample cut by the jaws is aspirated with the water. As the water is aspirated it passes through the chamber and the sample is filtered onto the screen. The screen may easily be removed to retrieve the sample. It will be further appreciated that the entire procedure of cutting a sample and retrieving the sample may be performed without removing the endoscopic biopsy forceps instrument from its location within the body.

According to one embodiment of the biopsy forceps instrument, the tubular member is ovoid in shape and defines a control conduit, an irrigation conduit, and an aspiration conduit. The distal forceps assembly includes a movable jaw, and a substantially rigid molded collar which is provided with a proximal socket-like coupling means for coupling the tubular member thereto, a fixed jaw cup, a distal irrigation passage, and a control passage. The collar is of similar diameter to the endoscope and is designed to be coupled to the outside of the distal end of an endoscope by a silicone rubber sock. The movable jaw is pivotally mounted on the molded collar and is movable relative to jaw cup. The tubular member is coupled in the socket. A control wire extends through the control conduit and the control passage is coupled to the two holes in the movable jaw.

According to a second embodiment, the biopsy forceps instrument includes a tubular member which defines an aspiration conduit having a circular cross section, an irrigation conduit having a kidney-shaped cross section, and two control conduits. The distal assembly includes a stationary jaw bonded to the distal end of the tubular member, and a movable jaw. The stationary jaw includes a hollow jaw cup, a clevis member and two proximal ramps. The jaw cup is located over the aspiration conduit, and the clevis and the proximal ramps extend from the jaw cup over the irrigation conduit. The movable jaw is coupled to the clevis and is guided along the proximal ramps. The two control conduits exit the distal end of the tubular member lateral of the proximal ramps. A central portion of a control member is coupled to the movable jaw and each end of the control member extends through the control conduits to the proximal end of the instrument.

According to a third embodiment of the biopsy forceps instrument, the instrument includes a tubular member which defines an aspiration conduit having a circular cross section and an irrigation conduit having a crescent-shaped cross section. The distal assembly is substantially similar to the second embodiment. The proximal ramps abut and partially cover the irrigation conduit to define two entrances into the irrigation conduit for the control members. A distal end of each control member is coupled to the movable jaw and the control members extend through the entrances and into the irrigation conduit. The entrances are sufficiently small such that when the jaws are in a closed position and fluid is irrigated through the irrigation conduit to the distal assembly, substantially all of the fluid passes through the irrigation conduit and into the jaws; i.e. only an insubstantial amount of the fluid irrigated through the irrigation conduit exits through the entrances formed by the ramps.

Additional objects and advantages of the invention will become apparent to those skilled in the art upon reference to the detailed description taken in conjunction with the provided figures.

BRIEF DESCRIPTION OF THE DRAWINGS

FIG. 2 is a broken perspective view of the proximal end of the first embodiment of the invention;

FIG. 3 is a broken perspective view of the sample chamber of the first embodiment of the invention;

FIG. 4 is a perspective view of the front side of the sample catch member of the first embodiment of the invention;

FIG. 5 is a perspective view of the back side of the sample catch member of the first embodiment of the invention;

FIG. 6 is an enlarged broken perspective view of the tubular member of the first embodiment of the invention;

FIG. 10 is a cross section across line 10—10 of FIG. 7;

FIG. 11 is cross section across line 11—11 of FIG. 8;

FIG. 12 is a broken perspective view of the distal assembly of the first embodiment illustrating an alternate control member configuration;

FIG. 13 is a broken perspective view of the distal assembly of the first embodiment illustrating another alternate control member configuration;

FIG. 15 is an enlarged broken transparent perspective view of the tubular member of the second embodiment of the invention;

FIG. 21 is an enlarged broken transparent perspective view of the tubular member of the third embodiment of the invention;

FIG. 22 is an enlarged cross-section across line 22—22 of FIG. 21; and

DETAILED DESCRIPTION OF THE PREFERRED EMBODIMENTS

Figure 1:
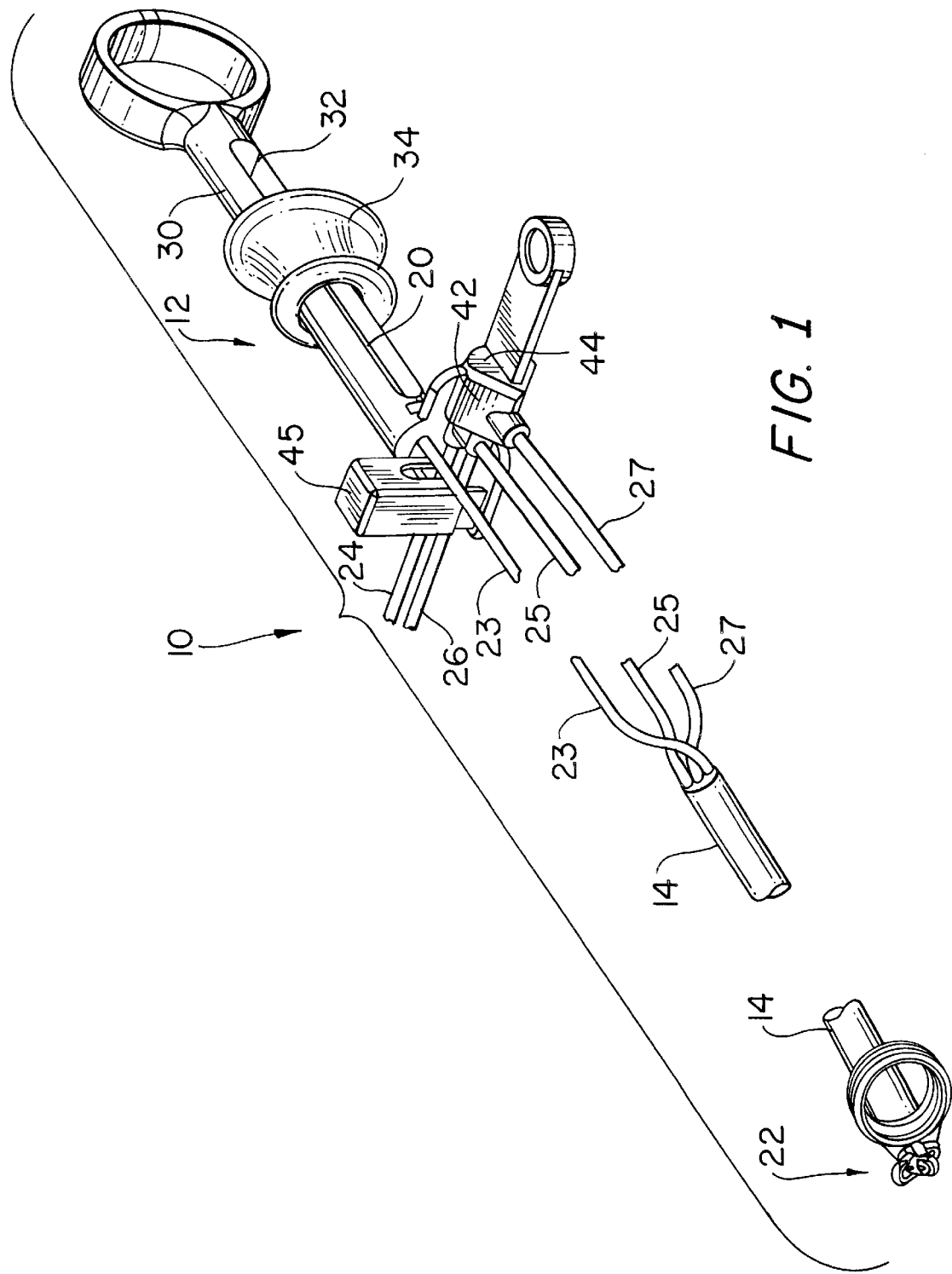
FIG. 1 is a broken perspective view of a first embodiment of an endoscopic biopsy forceps instrument according to the invention.

Turning now to FIG. 1, a multiple sample biopsy forceps instrument 10 is shown. The biopsy forceps instrument generally includes a proximal actuation handle 12, a flexible multi-lumen tubular member 14, a pull wire 20, and a distal assembly 22. Several coupling tubes are preferably provided to couple the proximal actuation handle 12 to the tubular member 14 and to irrigation and aspiration means. In particular, a control coupling tube 23, first and second irrigation coupling tubes 24, 25 and first and second aspiration coupling tubes 26, 27 are provided.

The proximal actuation handle 12 includes a shaft 30 having a transverse slot 32 and a spool 34 slidably mounted on the shaft and having a transverse bar (not shown) extending through the slot 32, as is common in the art. The actuation handle 12 is provided with a sample chamber 42, a sample catch member 44, and a pinch valve 45 which regulates irrigation and aspiration. Turning to FIG. 2, the sample chamber 42 includes irrigation connectors 46, 47 which couple the first irrigation coupling tube 24 to the second irrigation coupling tube 25. The sample chamber 42 also includes first and second aspiration connectors 48, 49 which couple the first aspiration coupling tube 26 to the second aspiration coupling tube 27. Referring to FIGS. 3 through 5, the sample catch member 44 includes a handle portion 52, an engagement portion 54 which removably engages the sample catch member 44 to the sample chamber 42, and a screen 56. The screen 56 extends through the sample chamber 42 between the first and second aspiration connectors 48, 49. The screen 56 includes a front side 58 and a back side 60 and is provided with a plurality of perforations 62 which are preferably frustoconical in shape and expand from the front side 58 to the back side 60. The first irrigation coupling tube 26 and the first aspiration coupling tube 27 extend through the pinch valve 45 which operates to control the flow of fluid through the tubes 26, 27. The pinch valve is biased to clamp closed the first irrigation coupling tube 26 and the first aspiration coupling tube 27, i.e., to collapse the tubes on top of each other. Pressing downward on the pinch valve 45 with a practitioner's finger counters the bias of the pinch valve to permit fluid flow through the first irrigation coupling tube 26 and the first aspiration coupling tube 27.

Figure 7:
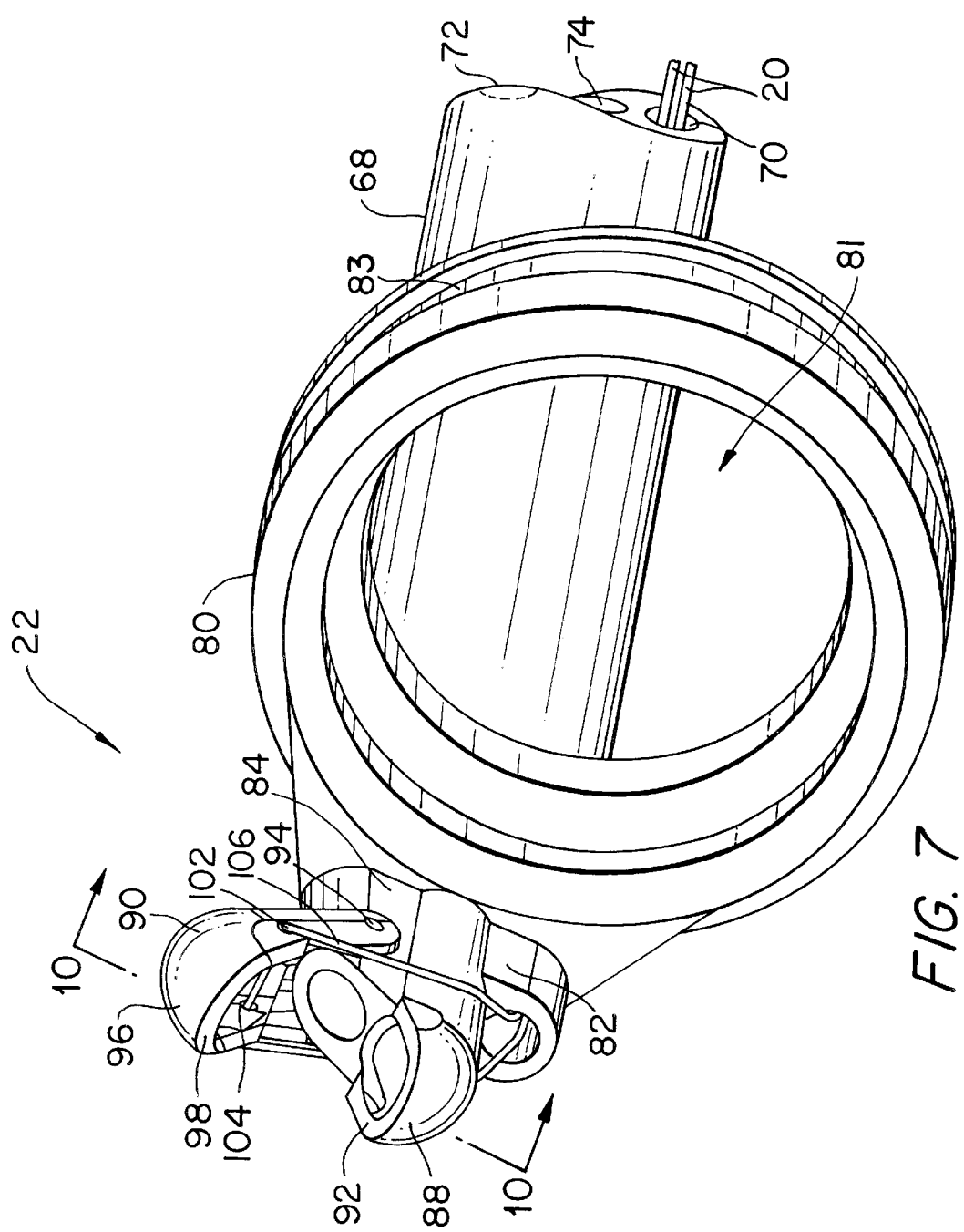
FIG. 7 is an enlarged broken perspective view of the distal assembly of the first embodiment of the invention with the jaws in an open position.

Turning to FIGS. 6 and 7, and in accord with the first embodiment of the invention, the tubular member 14 is preferably an ovoid multi-lumen extrusion. The tubular member includes a proximal end 66, a distal end 68, a control conduit 70, an irrigation conduit 72, and an aspiration conduit 74, each of which extends through the tubular member to the distal assembly 22. At the proximal end 66 of the tubular member, the control conduit 70 is coupled to the control coupling tube 23, the irrigation conduit 72 is coupled to the second irrigation coupling tube 25 and the aspiration conduit 74 is coupled to the second aspiration coupling tube 27.

Figure 9:
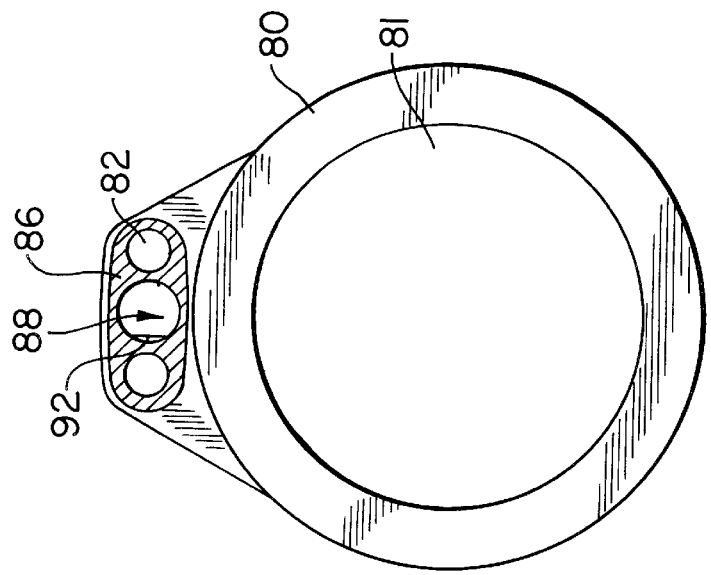
FIG. 9 is a bottom end view of FIG. 8.
Figure 8:
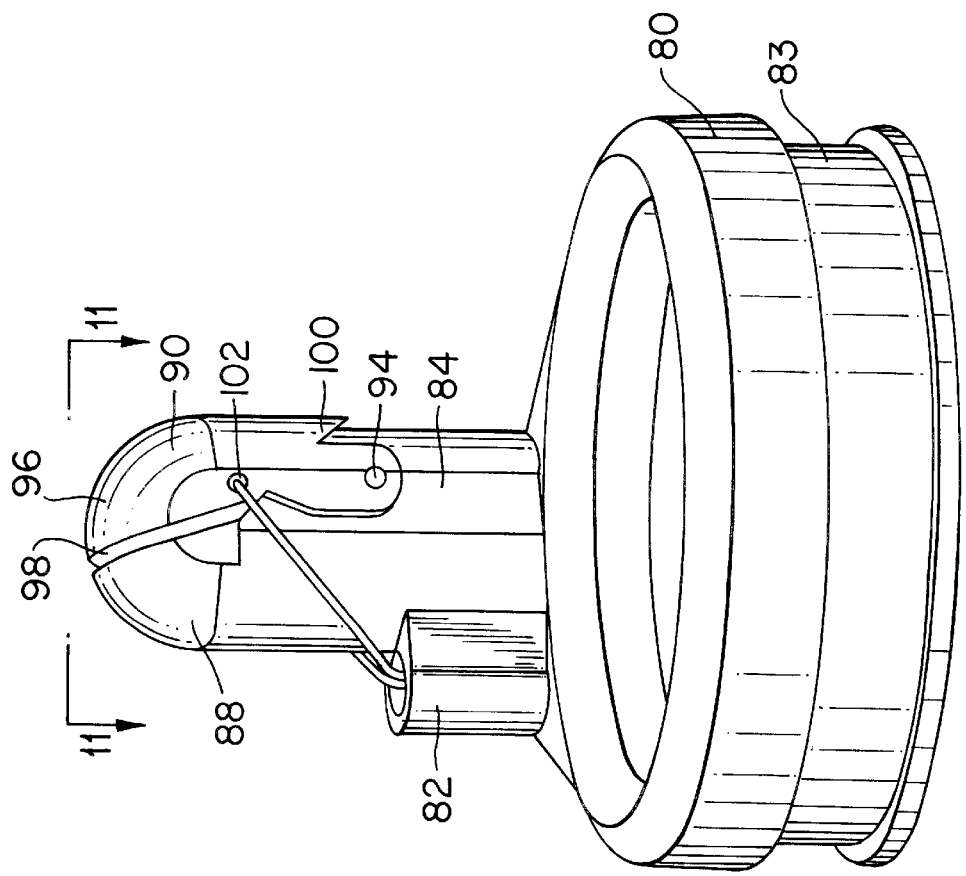
FIG. 8 is an enlarged broken perspective view of the distal assembly of the first embodiment of the invention with the jaws in a closed position.

Referring to FIGS. 7 through 9, the distal assembly 22 includes a substantially rigid molded collar 80 and a hollow movable jaw 90. The collar 80 is preferably made from a unitary piece of polycarbonate, a glass-filled polycarbonate, a hard grade styrene, or other plastic, while the movable jaw 90 is preferably made from cast metal. The collar includes a central opening 81, a circumferential channel 83, a distally extending control passage 82, a distally extending hollow jaw mount 84, a distally extending hollow stationary jaw 88, and a proximal socket 86. The central opening 81 of the collar 80 is of similar diameter to the outer diameter of the endoscope and is designed to couple the collar to the outside of the distal end of an endoscope. The circumferential channel 81 receives a portion of a silicone rubber sock (not shown), which is used to secure the collar 80 to the endoscope.

The stationary jaw 88 preferably includes a blunt edge or lip 92. The movable jaw 90 is pivotally mounted at a pivot 94 on the jaw mount 84 and is pivotable relative to stationary jaw 88. The movable jaw 90 is preferably provided with a sharp cutting edge 98, a stop 100 for limiting the extent to which the movable jaw pivots away from the stationary jaw 88, and two jaw holes 102, 104, for receiving a pull wire 20, as described below.

Referring to FIGS. 9 through 11, the proximal socket 86 is aligned with the control passage 82, the jaw mount 84 and the stationary jaw 88, and is designed to receive the distal end 68 of the flexible tubular member 14. The distal end 68 of the tubular member is secured in the proximal socket 86, preferably using an adhesion bonding agent, such that the control passage 82 is coupled to the control conduit 70, the jaw mount 84 is coupled substantially fluidtight to the irrigation conduit 72, and the stationary jaw 88 is coupled substantially fluidtight to the aspiration conduit 76.

Turning back to FIGS. 1, 6, 7 and 10, a central portion of the pull wire 20 extends through the jaw holes 102, 104 and the ends of the pull wire 20 extend through the control passage 82, the control conduit 70, and the control coupling tube 23 to the spool 34. Referring to FIG. 12, alternatively the pull wire 20a forms a secure loop 106a through the jaw holes 102a, 104a by doubling back on itself and forming a twist 108a. Referring to FIG. 13, in yet another alternative, two pull wires 20b, 21b may be used, the distal end of each pull wire being coupled to a jaw hole 102b, 104b by a Z-bend 110b, 112b and extending through the control passage 82b.

Referring to FIGS. 1, 7, and 8, it will be appreciated that movement of the spool 34 relative to the shaft 30 results in movement of the pull wire 20 relative to the tubular member 14 and consequently moves the movable jaw 90 relative to the stationary jaw 88 such that the jaws open (FIG. 7) and close (FIG. 8). Referring to FIGS. 7 through 11, when the stationary and movable jaws 88, 90 are in a closed position a substantially fluidtight passage is formed therebetween. Because the stationary jaw 88 is coupled to the aspiration conduit 74 and the movable jaw 90 is coupled over the irrigation conduit 72, a substantially fluidtight coupling of the irrigation and aspiration conduits is achieved.

In use, it will be appreciated that the distal end of the endoscope to which the collar 80 is coupled is maneuvered adjacent the desired tissue for sampling and the distal assembly is brought into contact with tissue 110 (FIGS. 10 and 11). The actuation handle 12 is actuated to close the jaws 88, 90 and cut off a tissue sample 112. When the jaws 88, 90 are in a closed position, the irrigation means and the aspiration means are activated and the first proximal irrigation coupling tube and the first proximal aspiration coupling tube 24, 26 are released from the clamping action of the pinch valve 45 by depressing the pinch valve. Irrigating fluid is thereby permitted to flow through the first and second proximal irrigation coupling tubes 24, 26, through the irrigation conduit 72 and the hollow jaw mount 84, and to the jaws 88, 90 at the distal end of the instrument. The fluid flows through the jaws and is aspirated back to the proximal end of the instrument such that the sample held within the jaws is aspirated with the water. Turning back to FIGS. 2 through 6, as the water is aspirated through the aspiration conduit 74 and into the sample chamber 42, the sample is filtered onto the screen 58. The frustoconical shape of the perforations 62 permits increased fluid flow through the perforate screen while preventing the tissue sample from passing through the screen. Irrigation and aspiration means are interrupted by releasing the pinch valve 45 such that the pinch valve clamps down on the first proximal irrigation and aspiration coupling tubes 24, 26 and causes the tubes to collapse on top of each other. The screen 58 may easily be removed to retrieve the sample by gripping the handle portion 52 of the sample catch member 44 and pulling the sample catch member from the sample chamber 42. The sample is recovered from the screen, and the sample catch member is reinserted into the sample chamber to continue the procedure. It will be further appreciated that the entire procedure of cutting a sample and retrieving the sample may be performed without removing the endoscopic multiple sample biopsy forceps instrument from its location within the body. Unlimited subsequent samples may be obtained in an identical manner.

Figure 14:
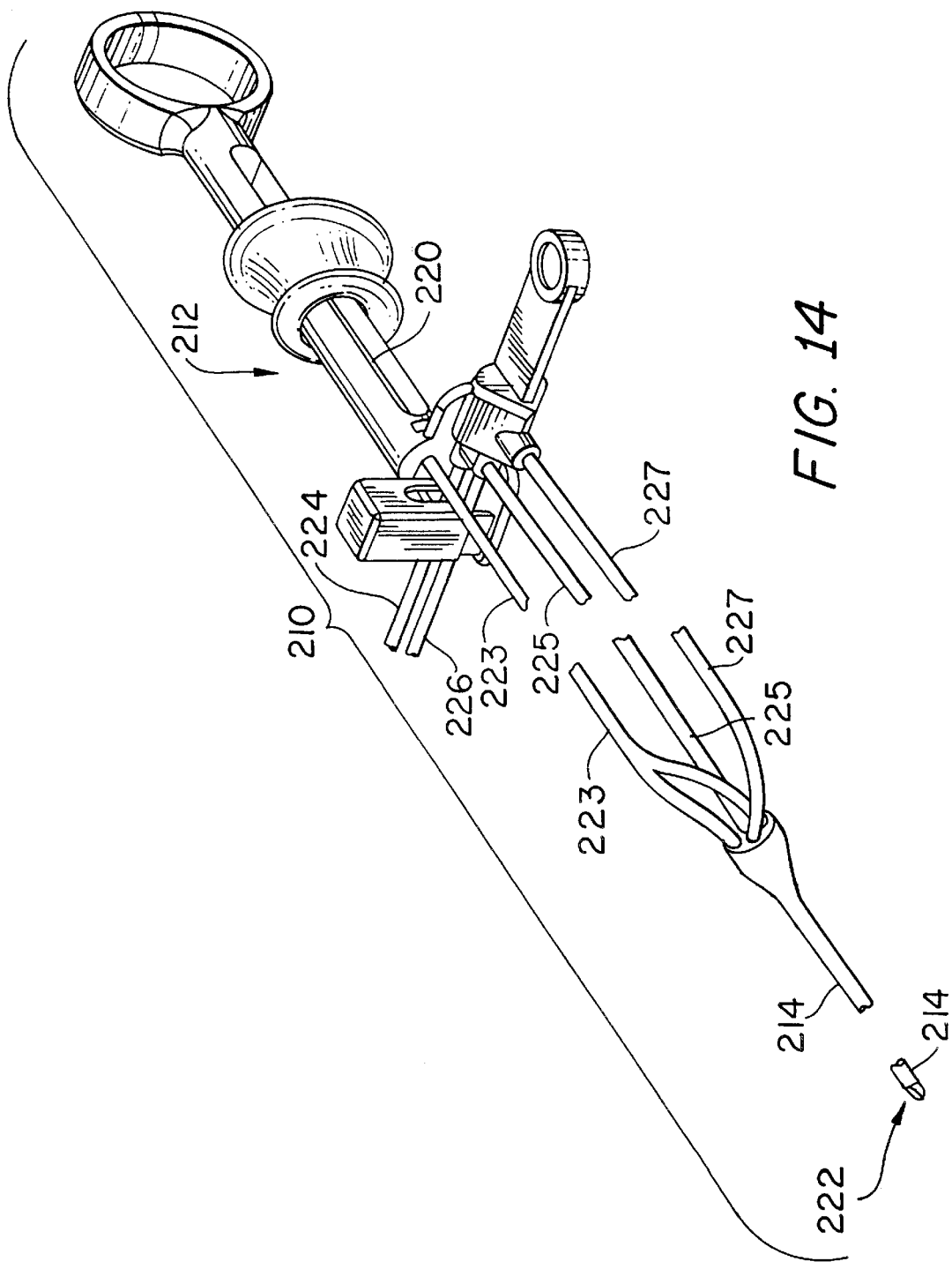
FIG. 14 is a broken perspective view of a second embodiment of an endoscopic biopsy forceps instrument of the invention.

Turning to FIGS. 14 and 15, a second embodiment of a multiple sample biopsy forceps instrument 210 is shown. The instrument includes a proximal actuation handle 212, a flexible multi-lumen tubular member 214, a pull wire 220, and a distal assembly 222. Several coupling tubes are preferably provided to couple the proximal actuation handle 212 to the tubular member 214 and to irrigation and aspiration means. In particular, a Y-shaped control coupling tube 223, first and second irrigation coupling tubes 224, 225, and first and second aspiration coupling tubes 226, 227 are provided.

Figure 16:
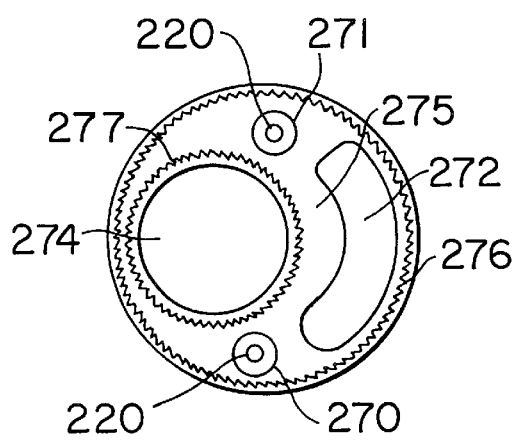
FIG. 16 is an enlarged cross section across line 16—16 of FIG. 15.
Figure 17:
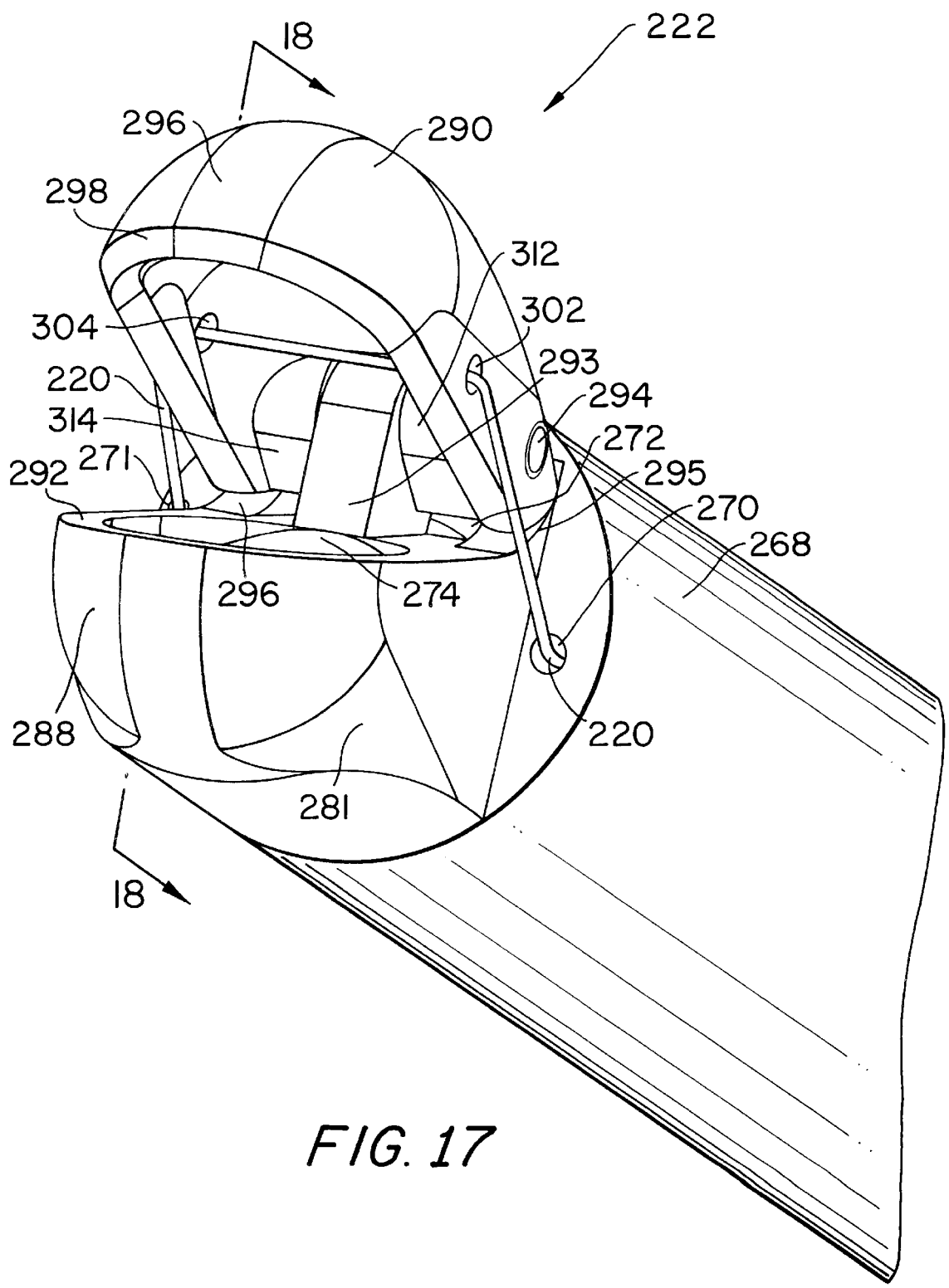
FIG. 17 is an enlarged broken perspective view of the distal assembly of the second embodiment of the invention with the jaws in an open position.
Figure 19:
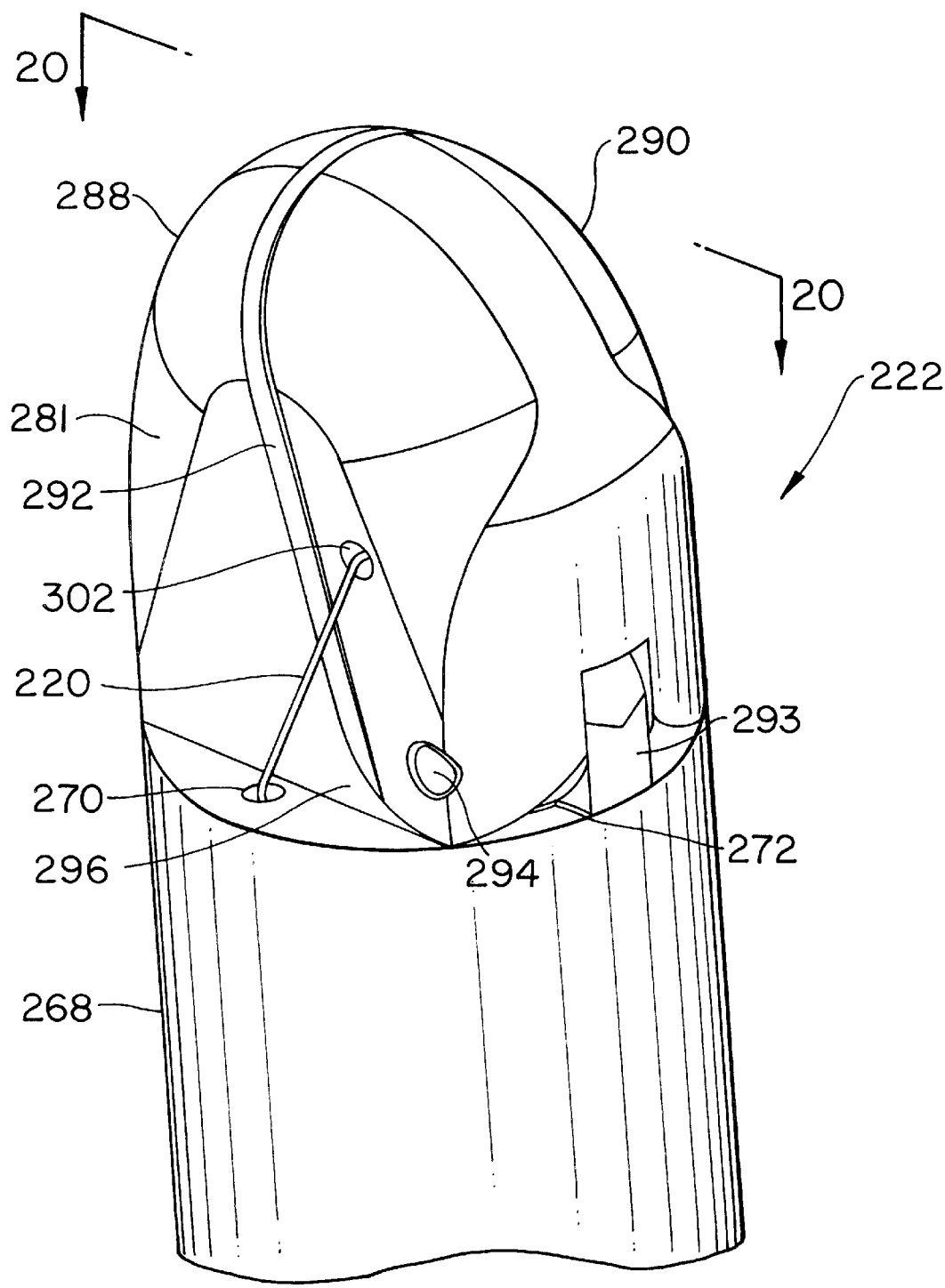
FIG. 19 is an enlarged broken perspective view of the distal end of the second embodiment of the invention with the biopsy jaws in a closed position.

The proximal actuation handle 212 is substantially similar to the first embodiment (with like parts having numbers incremented by 200). Referring to FIGS. 15, 16 and 17, the tubular member 214 is preferably a multi-lumen multi-layer extrusion, and preferably includes a first metal braid 276 beneath the outermost layer to add desired stiffness to the tubular member. If desired, a second metal braid 277 may be additionally provided around the aspiration conduit 274 to stiffen and support the aspiration conduit 274. The tubular member 214 has a proximal end 266, a distal end 268, two control conduits 270, 271, an irrigation conduit 272, and an aspiration conduit 274, each of the conduits 270, 271, 272, 274 extending through the tubular member to the distal assembly 222. The aspiration conduit 274 has a substantially circular cross section. The irrigation conduit 272 has a generally kidney-shaped cross section and is separated from the aspiration conduit 274 by a membrane 275. The control conduits 270, 271 are preferably situated one on either end of the membrane 275.

Referring to FIGS. 17 through 20, the distal assembly 222 according to the second embodiment of the invention includes a stationary jaw 281 coupled, preferably by adhesion bonding, to the distal end 268 of the tubular member. The stationary jaw 281, preferably made of plastic, includes a jaw cup 288, an integral central clevis 293 and integral proximal ramps 295, 296. The jaw cup 288 is located over the aspiration conduit 274 and preferably has a blunt cutting surface or lip 292. The central clevis 293 and proximal ramps 295, 296 extend from the stationary jaw 281 and abut and partially cover the irrigation conduit. A movable jaw 290, preferably made of metal, is provided with a sharp cutting edge 298, defines two jaw holes 302, 304 for receiving a pull wire 220, and is provided with two bosses 312, 314 for mounting the jaw. The bosses 312, 314 loosely engage the central clevis 293 and a pivot pin 294 extends through the bosses and the central clevis. The ramps 295, 296 of the stationary jaw 281 guide the movable jaw 290 when opening and closing and assist to form a substantially fluidtight passage between the movable jaw 290 and the stationary jaw cup 288 when the jaws are in a closed position. A central portion of the pull wire 220 which is perpendicular to the longitudinal axis of the instrument extends through the jaw holes 302, 304 and the ends of the pull wire extend into the control conduits 270, 271. Turning back to FIG. 15, the Y-shaped coupling tube 223 facilitates alignment of the ends of the pull wire 220 for coupling the pull wire to the proximal actuation handle. The pull wire 220 may be coated, e.g., in a plastic, to inhibit the pull wire from cutting into the tubular member.

Figure 20:
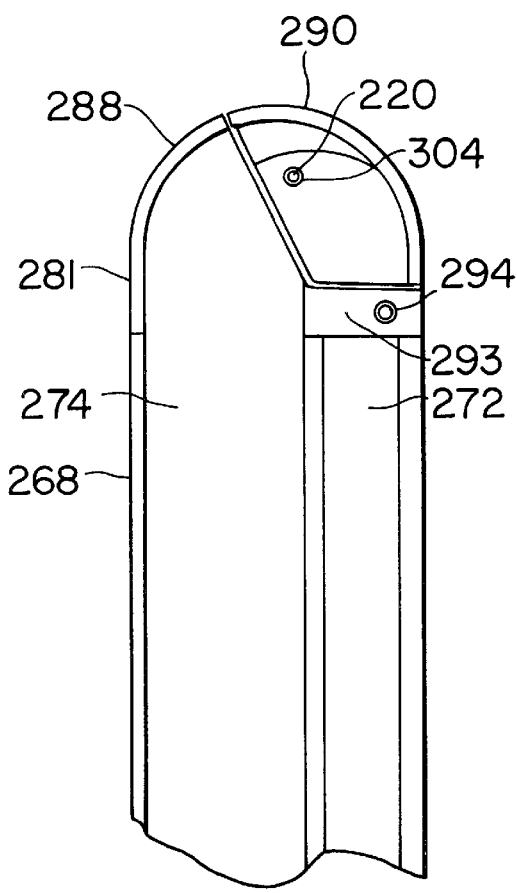
FIG. 20 is a cross section across line 20—20 of FIG. 19.
Figure 18:
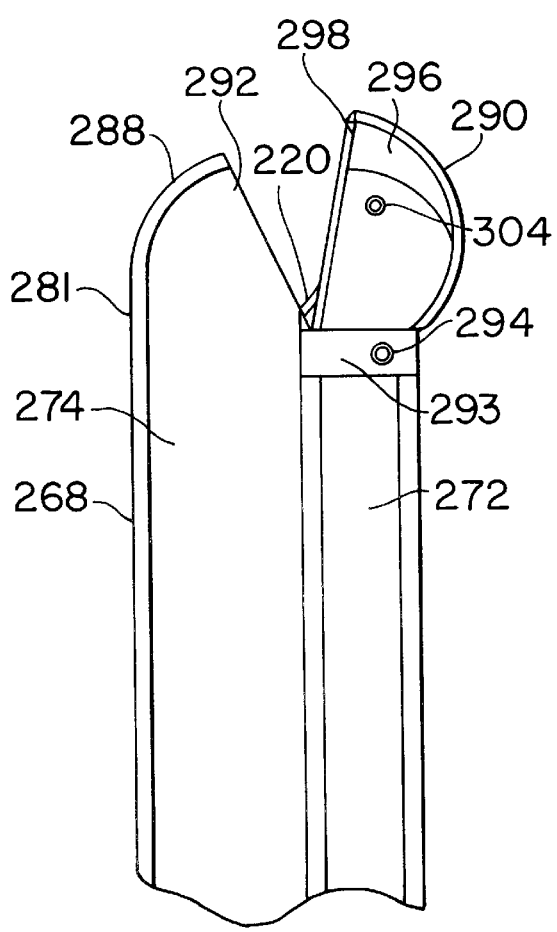
FIG. 18 is a cross section across line 18—18 of FIG. 17.

Referring to FIGS. 18 and 20, the distal end 268 of the tubular member is inserted through the lumen of an endoscope to a biopsy site. The jaws 288, 290 are moved into a closed position cutting off a tissue sample and further providing a substantially fluidtight coupling between the irrigation and aspiration conduits 272, 274. While it appears from the illustrations of FIGS. 18 and 20 that the irrigation conduit 272 is obstructed at the distal end by clevis 293, it will be appreciated that the irrigation conduit 272 is substantially wider than the clevis and that fluid may flow around the clevis to the aspiration conduit 274.

Figure 23:
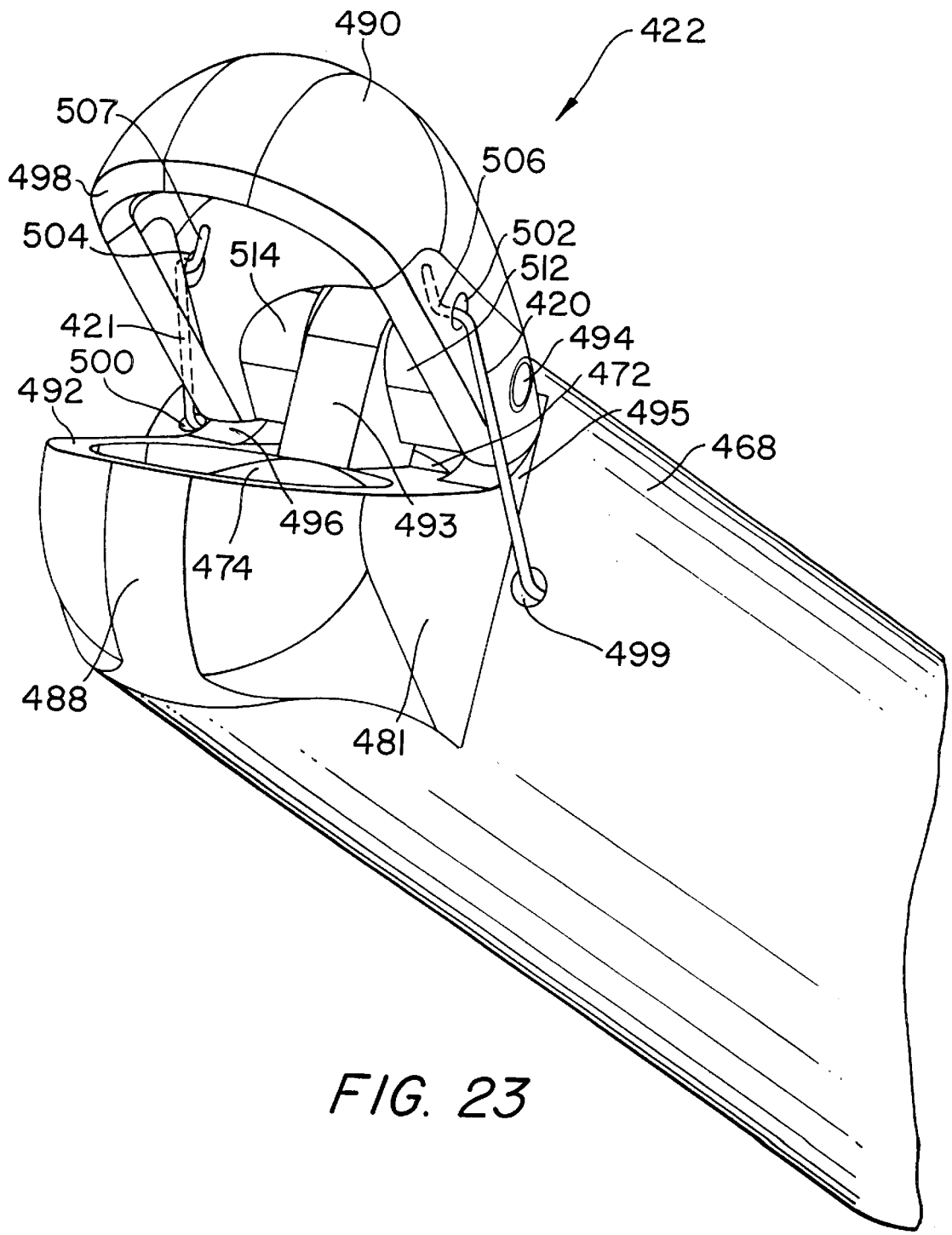
FIG. 23 is a enlarged broken perspective view of the distal end of a third embodiment of the invention with the jaws in an open position.

Turning now to FIGS. 21 through 23, a third embodiment of a multiple sample biopsy forceps, substantially similar to the second embodiment (with like parts having numbers incremented by another 200) is shown. The tubular member 414 has a proximal end 466, a distal end 468, an irrigation conduit 472, and an aspiration conduit 474. The aspiration conduit 474 has a substantially circular cross section, while the irrigation conduit 472 has a generally crescent-shaped cross section. A control coupling tube 423 is coupled to the second irrigation coupling tube 425. Two pull wires 420, 421 extend through the control coupling tube 423, pass through a substantially fluidtight valve (not shown) coupling the control coupling tube 423 and the second irrigation coupling tube 425, enter into the second irrigation coupling tube 425, and extend through the irrigation conduit 472 to the distal end 468 of the tubular member. An aspiration coupling tube 427 is coupled to the aspiration conduit 474.

Referring to FIG. 23, the distal assembly 422 of the third embodiment of the invention includes a stationary jaw 481 bonded to the distal end 468 of the tubular member, and a movable jaw 490 coupled thereto. The stationary jaw 481 includes a jaw cup 488, an integral central clevis 493, and ramps 495, 496. The jaw cup abuts the distal end of the tubular member and is positioned over the aspiration conduit 474 and preferably has a blunt cutting surface or lip 492. The central clevis 493 and ramps 495, 496 extend from the stationary jaw 481 and abut and partially cover the irrigation conduit 474. A movable jaw 490, preferably made of metal, is provided with a sharp cutting edge 498, defines two jaw holes 402, 404 for receiving a pull wire 420, and is provided with two bosses 512, 514 for mounting the jaw. The bosses 512, 514 loosely engage the central clevis 493 and a pivot pin 494 extends through the bosses and the central clevis. By partially covering the irrigation conduit, the ramps form entrances 499, 500 for the pull wires, as described below. The movable jaw 490 rides on the proximal ramps 495, 496 when moving from an open to a closed position. The pull wires 420, 421 are coupled to the jaw holes 502, 504 by a Z-bend 506, 507 and extend through the entrances 499, 500 into the irrigation conduit 472, through a portion of the second irrigation coupling tube 425, and further into a control coupling tube 423 coupled thereto. The entrances 499, 500 are sufficiently small that only an insubstantial amount of fluid exits from the irrigation conduit when the jaws are in a closed position and irrigant is forced through the irrigation conduit 474 to the distal assembly.

There have been described and illustrated herein several embodiments of a multiple sample endoscopic biopsy instrument. While particular embodiments of the invention have been described, it is not intended that the invention be limited thereto, as it is intended that the invention be as broad in scope as the art will allow and that the specification be read likewise. Therefore, while a particular manner of coupling the proximal actuation handle to the distal assembly has been disclosed for the several embodiments, it will be appreciated that other manners of coupling the proximal and distal assemblies may be used as well. Furthermore while the stationary jaw is disclosed as preferably being made of plastic and the movable jaw is disclosed as being made of metal it will be appreciated both the stationary jaw and the movable jaw may be made from plastic, metal, or another material. Moreover, while the movable jaw is disclosed as preferably being made from cast metal, it will be appreciated that the movable jaw, when made of metal, may alternatively be made by machining or M.I.M. Further, while both jaws are shown without teeth, one or both of the jaws may include teeth along their mating surface. In fact, the teeth may be arranged radially as disclosed in co-owned U.S. Pat. No. 5,507,296. Also, while one or two pull wires are disclosed with respect to certain embodiments, it will be appreciated that in each embodiment either one or two pull wires may be used, in manners described herein. Furthermore, while the stationary jaw is disclosed as being coupled to the aspiration tube and the movable jaw is disclosed as being coupled to the irrigation conduit, it will be appreciated that the stationary jaw may be coupled to the irrigation conduit and the movable jaw may be coupled to the aspiration conduit. Moreover, it will be appreciated that both the jaws may be movable about the distal end of the tubular member. In addition, while particular configurations have been disclosed in reference to coupling the proximal actuation handle to the tubular member, it will be appreciated that other configurations can be used as well. It will therefore be appreciated by those skilled in the art that yet other modifications could be made to the provided invention without deviating from its spirit and scope as so claimed.

We claim:

1. A biopsy forceps instrument for retrieving tissue samples from a patient for use with an endoscope, comprising:
   a) a flexible tubular member having an irrigation conduit and an aspiration conduit;
   b) a distal assembly having a hollow first jaw and a hollow movable second jaw, said movable second jaw being pivotable relative to said first jaw and coupled to at least one of said irrigation conduit and said aspiration conduit, and said first jaw being coupled to another of said at least one of said irrigation conduit and said aspiration conduit; and
   c) a proximal actuator coupled to said distal assembly for moving said movable second jaw relative to said first jaw from an open position to a closed position to obtain a tissue sample from the patient, and wherein said movable second jaw and said first jaw are adapted such that when said movable second jaw and first jaw are in said closed position, said movable second jaw and first jaw form a substantially closed fluid passage between said irrigation conduit and said aspiration conduit so that the aspiration conduit can retrieve the tissue sample from the distal assembly with irrigation fluid provided by the irrigation conduit.

2. A biopsy forceps instrument according to claim 1, further comprising:
   at least one control member coupled to said movable second jaw, wherein the proximal actuator is coupled to the at least one control member for moving said at least one control member relative to said tubular member thereby moving said movable second jaw relative to said first jaw, said at least one control member extending through said flexible tubular member.

3. A biopsy forceps instrument according to claim 2, wherein:
   said tubular member has a control conduit, said at least one control member extending through said control conduit.

4. A biopsy forceps instrument according to claim 1, wherein:
   said first jaw is stationary.

5. A biopsy forceps instrument according to claim 4, wherein:
   said first jaw is coupled to said aspiration conduit and said movable second jaw is coupled to said irrigation conduit.

6. A biopsy forceps instrument according to claim 5, wherein:
   said tubular member has a control conduit and at least one control member extends through said control conduit.

7. A biopsy forceps instrument according to claim 1, further comprising:
   e) a collar coupled to said distal assembly, said collar adapted to couple said distal assembly to the endoscope.

8. A biopsy forceps instrument according to claim 7, wherein:
   said collar is integral with said first jaw.

9. A biopsy forceps instrument according to claim 7, wherein:
   said collar includes a proximal socket for receiving said tubular member.

10. A biopsy forceps instrument according to claim 1, wherein:
    said movable second jaw is provided with a stop which limits rotation of said movable second jaw relative to said first jaw.

11. A biopsy forceps instrument according to claim 1, wherein:
    said first jaw is made of plastic and said movable second jaw is made of metal.

12. A biopsy forceps instrument according to claim 1, wherein:
    said first jaw has a substantially flat lip, and said movable second jaw ha s a sharp cutting edge.

13. A biopsy forceps instrument according to claim 1, wherein:
    said movable second jaw is provided with two jaw holes and at least one control member extends through said two jaw holes.

14. A biopsy forceps instrument according to claim 13, wherein:
    said tubular member has a control conduit and said control member extends through said control conduit and said jaw holes to form a loop.

15. A biopsy forceps instrument according to claim 13, wherein:
    said control member has a central portion and two ends, wherein said central portion extends through said two jaw holes and said two ends are coupled to said proximal actuator.

16. A biopsy forceps instrument according to claim 13, wherein:
    said at least one control member includes two control members, each of said two control members having a first and second end, said first end of each of said two control members forms a Z-bend through one of said two jaw holes.

17. A biopsy forceps instrument according to claim 1, wherein:
    said fluid passage is substantially fluidtight so as to be capable of limiting fluid that exits the distal assembly to the patient when the movable second jaw and first jaw are in said closed position.

18. A biopsy forceps instrument according to claim 1, wherein:
    said tubular member is substantially ovoid.

19. A biopsy forceps instrument according to claim 1, further comprising:
    e) a clevis coupled to a distal end of said tubular member, wherein said movable second jaw is coupled to said clevis.

20. A biopsy forceps instrument according to claim 19, wherein:
    said clevis partially covers said distal end of said irrigation conduit.

21. A biopsy forceps instrument according to claim 19, wherein:
    said irrigation conduit has a generally kidney-shaped cross section.

22. A biopsy forceps instrument according to claim 19, wherein:

said irrigation conduit has a generally crescent-shaped cross section.

23. A biopsy forceps instrument according to claim 19, wherein:

said tubular member is a multi-layer extrusion having an outermost layer.

24. A biopsy forceps instrument according to claim 23, wherein:

said tubular member is provided with at least one of a first metal braid around said aspiration conduit and a second metal braid under said outermost layer of said tubular member.

25. A biopsy forceps instrument, comprising:

a) a flexible tubular member having proximal and distal ends;

b) at least one control member extending through said tubular member;

c) a first jaw cup coupled to said distal end of said tubular member and having top surface formed as a blunt lip;

d) a movable second jaw cup movable relative to said first jaw cup and having a sharp cutting surface; and e) a proximal actuator coupled to said at least one control member for moving said at least one control member relative to said tubular member, and thereby moving said second jaw cup relative to said first jaw cup from an open position to a closed position;

wherein in said closed position said sharp cutting surface of said movable second jaw cup abuts said blunt lip of said first jaw cup.

26. A biopsy forceps instrument according to claim 25, wherein:

said first jaw cup is stationary relative to said flexible tubular member.

27. A biopsy forceps instrument according to claim 25, wherein:

said first jaw is made of plastic.

28. A biopsy forceps instrument according to claim 25, wherein:

said movable second jaw is made of metal.

29. A biopsy forceps instrument according to claim 19, wherein:

said first jaw is adhesion bonded to a distal end of said of tubular member.

* * * * *

UNITED STATES PATENT AND TRADEMARK OFFICE
CERTIFICATE OF CORRECTION

PATENT NO. : 5,897,507

DATED : April 27, 1999

INVENTOR(S) : Juergen A. KORTENBACH et al.

It is certified that error appears in the above-indentified patent and that said Letters Patent is hereby corrected as shown below:

Claim 12, col. 12, line 21, "ha s a" should be --has a--.

Claim 19, col. 12, line 57, "e)" should be --d)--.

Signed and Sealed this

Twenty-sixth Day of October, 1999

Attest:

Q. TODD DICKINSON

*Attesting Officer*  *Acting Commissioner of Patents and Trademarks*